(12) United States Patent
Balashanmugam et al.

(10) Patent No.: US 10,794,891 B2
(45) Date of Patent: Oct. 6, 2020

(54) FUEL OIL STABILITY

(71) Applicant: BP Corporation North America Inc., Houston, TX (US)

(72) Inventors: Soban Balashanmugam, Surrey (GB); Rosa Rueda-Velasquez, Naperville, IL (US)

(73) Assignee: BP Corporation North America Inc., Naperville, IL (US)

( * ) Notice: Subject to any disclaimer, the term of this patent is extended or adjusted under 35 U.S.C. 154(b) by 0 days.

(21) Appl. No.: 15/824,453

(22) Filed: Nov. 28, 2017

(65) Prior Publication Data

US 2018/0156772 A1 Jun. 7, 2018

Related U.S. Application Data

(60) Provisional application No. 62/428,748, filed on Dec. 1, 2016.

(51) Int. Cl.
*G01N 33/28* (2006.01)
*C10G 75/00* (2006.01)

(52) U.S. Cl.
CPC ......... *G01N 33/2823* (2013.01); *C10G 75/00* (2013.01); *G01N 33/2829* (2013.01); *G01N 33/2835* (2013.01); *C10G 2300/107* (2013.01); *C10G 2300/1077* (2013.01); *C10G 2300/206* (2013.01); *C10G 2300/30* (2013.01); *C10G 2400/06* (2013.01)

(58) Field of Classification Search
CPC .............. C10G 75/00; G01N 33/2823; G01N 33/2829; G01N 33/2835
See application file for complete search history.

(56) References Cited

U.S. PATENT DOCUMENTS

| | | | |
|---|---|---|---|
| 7,618,822 B2 | 11/2009 | Nemana et al. | |
| 2013/0124105 A1* | 5/2013 | Rogel | G01N 33/2823 702/25 |
| 2016/0216191 A1* | 7/2016 | Balashanmugam | G01N 33/2823 |
| 2017/0227434 A1* | 8/2017 | Respini | G01N 13/00 |
| 2017/0261446 A1* | 9/2017 | Adam-Berret | G01N 24/085 |

* cited by examiner

*Primary Examiner* — Renee Robinson
(74) *Attorney, Agent, or Firm* — McDonnell Boehnen Hulbert & Berghoff LLP (57) ABSTRACT

A method for predicting the critical solvent power of a visbroken residue stream of interest, $CSP_{VisRes(OI)}$ comprises predicting $CSP_{VisRes(OI)}$ from the critical percentage titrant of an atmospheric residue stream, $CPT_{AR}$, the atmospheric residue stream being derived from the same crude oil as the visbroken residue stream of interest. A method for predicting the solvent power of a visbroken residue stream of interest, $SP_{VisRes(OI)}$, comprises predicting $SP_{VisRes(OI)}$ from the critical solvent power of the visbroken residue stream, $CSP_{VisRes}$, and the critical percentage titrant of the visbroken residue stream, $CPT_{VisRes}$. $CPT_{VisRes}$ is derived from the critical percentage cetane of the visbroken residue stream, $CPC_{VisRes}$, which, in turn, is calculated from the P-value of the visbroken residue stream. The methods may be used to predict the stability of a fuel oil containing the visbroken residue.

18 Claims, 4 Drawing Sheets

FUEL OIL STABILITY

The present invention relates to methods for predicting the solvent power and critical solvent power of a visbroken residue stream. The solvent power and critical solvent power of a visbroken residue stream may be used as part of a method for predicting the stability of a fuel oil.

BACKGROUND OF THE INVENTION

Visbreaking is a process in which heavy, viscous refinery streams such as vacuum residues, atmospheric residues and combinations thereof are subject to mild thermal conversion in a visbreaker unit (VSB). VSB feed is typically concentrated in compounds known as asphaltenes.

Asphaltenes are organic heterocyclic macro-molecules that usually represent the heaviest compounds in crude oil. Asphaltenes are defined as a solubility class and, whilst they are typically soluble in aromatic solvents such as toluene, they are insoluble in paraffinic solvents such as n-heptane. At high temperatures encountered in refineries, asphaltenes in the feed can become insoluble, resulting in precipitation and possible deposition e.g. on furnace tube surfaces.

Visbreaking results in the generation of a series of lighter and more valuable products (such as kerosene and gas oils) from relatively low value residue streams. The main product from a VSB is known as visbroken residue (vis res). Visbroken residue streams have many applications, including as the main component in the production of fuel oils for power generation (e.g. marine fuel oils for use in marine vessels). Visbroken residue streams may alternatively be subject to further conversion in a refinery (e.g. in a coker, partial oxidation unit etc.).

Marine fuel oil (also known as bunker fuel) is subject to stringent quality constraints including those relating to viscosity, contaminant content (e.g. Si, Al, Fe) and, importantly, the stability of the asphaltenes fraction in the fuel. Fuel oil batches, such as marine fuel oil batches, are typically tested for stability using the aged sediment specification, determined according to test method IP 390. In this method, a sample of the fuel is subjected to aggressive aging conditions (at 100° C. for 24 hours) and filtered to ensure that the total sediment levels in the fuel are below the threshold limit (0.05 or 0.1 wt %). If the sediment specification is met, then the fuel is generally deemed to be suitable for use in marine applications, provided that the other relevant fuel specifications, e.g. sulphur content, metals content, viscosity etc., are met.

The main visbreaking reactions include C—C bond scission, dehydrogenation, polymerisation and condensation. The overall impact of these reactions is an increase in the saturates (paraffin) content in the feed, a reduction in aromatics and resins content and a significant increase in the asphaltenes content. Attempts to increase the conversion or visbreaking severity (e.g. by higher furnace outlet temperatures, longer residence times) will generally result in the visbroken residue having:
  Increased asphaltene content. The condensation and polymerisation reactions are largely responsible for creating the asphaltenes during visbreaking. It is not unusual for asphaltenes content across a VSB to increase by 2-4 fold.
  Reduced solvent power (SP), due to the increased saturates and reduced aromatics/resins content. SP can be defined as the ability of a hydrocarbon stream to disperse and/or support asphaltenes (see e.g. US 2004/0121472).
  Increased asphaltene critical solvent power (CSPa). The CSPa is defined as the minimum solvent power required to keep asphaltenes in a hydrocarbon stream fully dispersed and in solution (see e.g. US 2004/0121472).

In cases where the SP of the visbroken residue falls below the CSPa, severe fouling and deposition of asphaltenes will take place, potentially in the VSB furnace tubes and the soaker drum. Conversely, if the SP of the visbroken residue falls above the CSPa, then furnace and soaker drum fouling is less likely. To avoid problems associated with asphaltene precipitation, an upper limit to conversion is therefore normally applied in the VSB.

However, problems with asphaltene precipitation can nonetheless occur downstream of the VSB. Whilst the visbroken residue stream from the VSB unit exhibits a lower viscosity relative to the feed material to the VSB, cutter stocks are often added to the visbroken residue stream to further reduce its viscosity in order to meet fuel oil specifications. Cutter stocks include materials such as naphtha, kerosene and gas oil streams, e.g. from a crude oil atmospheric distillation unit (CDU) in a typical refinery. Other cutter stocks include vacuum gas oils, e.g. produced from the vacuum distillation unit (VDU) and cycle oils from a Fluidised Catalytic Cracking (FCC) unit in a typical refinery.

Most "straight run" cutter stocks from a CDU such as kerosene, gas oils etc. tend to have low SP. Blending of cutter stocks with visbroken residue streams where the final blend SP falls below the CSPa will result in asphaltene incompatibility (i.e. larger asphaltene aggregates may form and start to precipitate). Refiners therefore attempt to ensure that a visbroken residue stream is used which has adequate stability reserve to permit cutter stock addition with the resulting blend meeting the required asphaltene stability specifications. However, careful selection of cutter stocks is nonetheless often required (e.g. FCC Light Cycle Oil (LCO) tends to have higher SP than CDU/VDU streams used as cutters).

Stability reserve is generally described using the "P-value" metric, as defined by test method SMS-1600-01. Typically VSBs are operated to obtain a visbroken residue stream that meets a target P-value, usually ranging from 1.05 to 1.20. Where marine fuel oil is the desired product, the VSB will generally be operated to give a visbroken residue stream with a relatively high P-value of 1.10 or more.

In sum, it is currently necessary to ensure that VSBs are operated so that: 1) the feed quality and operating conditions of the VSB unit do not result in excessive conversion and thus asphaltene instability during the visbreaking process; and 2) the visbroken residue stream produced has sufficient stability reserve to permit any cutter stock addition and pass final fuel stability tests, such as the IP 390 test.

There exists a need for a method which overcomes one or more of these constraints.

SUMMARY OF THE INVENTION

The present invention provides a method for predicting the critical solvent power of a visbroken residue stream of interest, $CSP_{VisRes(OI)}$, said method comprising:
  predicting $CSP_{VisRes(OI)}$ from the critical percentage titrant for asphaltene stability in an atmospheric residue stream, $CPT_{AR}$, the atmospheric residue stream being derived from the same crude oil as the visbroken residue stream of interest, using a correlation between the critical solvent power of a visbroken residue stream, $CSP_{VisRes}$, and the critical percentage titrant for asphaltene stability in an atmospheric residue stream, $CPT_{AR}$, wherein the correlation has been obtained by a method comprising:
for each of a plurality of crude oils, measuring:
$CSP_{VisRes}$ of a visbroken residue stream derived therefrom, and
$CPT_{AR}$ of an atmospheric residue stream derived therefrom, and
determining a correlation between $CSP_{VisRes}$ and $CPT_{AR}$.

Also provided is a method for predicting the solvent power of a visbroken residue stream of interest, $SP_{VisRes(OI)}$, said method comprising:
predicting $SP_{VisRes(OI)}$ using the following formula:

$$SP_{VisRes(OI)} = (100 \times CSP_{VisRes})/(100 - CPT_{VisRes})$$

wherein:
$CSP_{VisRes}$ is the critical solvent power of the visbroken residue stream, and
$CPT_{VisRes}$ is the critical percentage titrant (vol %) for asphaltene stability in the visbroken residue stream,
wherein $CPT_{VisRes}$ is derived from the critical percentage cetane (vol %) for asphaltene stability in the visbroken residue stream, $CPC_{VisRes}$ using the following formula:

$$CPT_{VisRes} = CF + CPC_{VisRes}$$

wherein: CF is a conversion factor that relates $CPT_{VisRes}$ to $CPC_{VisRes}$;
and wherein $CPC_{VisRes}$ is calculated from the P-value of the visbroken residue stream using the following formula:

$$CPC_{VisRes} = ([(P\text{-value}-1)*\rho_{VisRes}]/[((P\text{-value}-1)*\rho_{VisRes})+1])*100$$

wherein:
$\rho_{VisRes}$ is the density of the visbroken residue stream.

A method for predicting the stability of a visbroken residue stream is also provided, said method comprising:
comparing the solvent power of the visbroken residue stream, $SP_{VisRes}$, with the critical solvent power of the visbroken residue stream, $CSP_{VisRes}$, and categorising the visbroken residue stream as stable if $SP_{VisRes}$ is larger than $CSP_{VisRes}$,
wherein $CSP_{VisRes}$ is predicted using a method of the present invention and/or $SP_{VisRes}$ is predicted using a method of the present invention.

Also provided is a method for preventing the precipitation of asphaltenes from a visbroken residue stream, said method comprising:
predicting the stability of the visbroken residue using a method of the present invention, and
adjusting the refinery process to ensure that the visbroken residue meets the stability requirements where the visbroken residue is categorised unstable.

Also provided is a method for predicting the critical solvent power of a fuel oil, $CSP_{FO}$, the fuel oil containing n blend components including a visbroken residue stream, said method comprising:
predicting $CSP_{FO}$ using the following formula:

$$CSP_{FO} = \sum_{i=1}^{n} \frac{(Wt\ \%_i * Asp\ content_i)}{Asp\ content_{(FO)}} * CSP_i$$

wherein:
Wt $\%_i$ is the %, by weight, of each of the n blend components
Asp $content_i$ is the asphaltene content of each of the n blend components,
Asp $content_{(FO)}$ is the asphaltene content of the fuel oil, and
$CSP_i$ is the critical solvent power of each of the n fuel oils,
wherein the critical solvent power for the visbroken residue stream, $CSP_{VisRes}$, is predicted using a method of the present invention.

Also provided is a method for predicting the solvent power of a fuel oil, $SP_{FO}$, the fuel oil containing n blend components including a visbroken residue stream, said method comprising:
predicting $SP_{FO}$ using the following formula:

$$SP_{FO} = \sum_{i=1}^{n} Vol\ \%_i * SP_i$$

wherein:
Vol $\%_i$ is the % by volume of each of the n blend components in the fuel oil, and
$SP_i$ is the solvent power of each of the n blend components,
wherein the solvent power for the visbroken residue stream, $SP_{VisRes}$, is predicted using a method of the present invention.

Also provided is a method for predicting the stability of a fuel oil, said method comprising:
comparing the solvent power of the fuel oil, $SP_{FO}$, with the critical solvent power of the fuel oil, $CSP_{FO}$, and
categorising the fuel oil as stable if $SP_{FO}$ is larger than $CSP_{FO}$,
wherein $CSP_{FO}$ is predicted using a method of the present invention and/or $SP_{FO}$ is predicted using a method of the present invention.

Also provided is a method for preventing the precipitation of asphaltenes from a fuel oil, said method comprising:
predicting the stability of the fuel oil using a method of the present invention, and
adjusting the refinery process to ensure that the fuel oil meets the stability requirements where the fuel oil is categorised as unstable.

BRIEF DESCRIPTION OF THE DRAWINGS

FIG. 1 is a graph showing the correlation between the solvent power of cutter stocks, $SP_{CS}$, and the aromatics content of the cutter stocks;

DETAILED DESCRIPTION OF THE INVENTION

Cutter Stock (CS)

The cutter stock is blended with the visbroken residue stream in order to produce the fuel oil. The cutter stock principally functions to reduce the viscosity of the visbroken residue stream, so that the resulting fuel oil meets the required industry specifications.

The cutter stock may be selected from straight run distillates (e.g. naphtha, kerosene, and gas oils such as vacuum gas oil), and cracked products (e.g. FCC cycle oils, and FCC slurry). These common refinery streams are known to the skilled person, and will generally have the following boiling ranges (measured under standard atmospheric pressure of 100 kPa): naphtha from 70 to 150° C.; kerosene from 120 to 220° C.; gas oil from 180 to 350° C.; vacuum gas oil from 300 to 580° C.; cycle oil from 250 to 450° C.; and FCC slurry from 400 to 580° C.

The solvent power of the cutter stock, $SP_{CS}$, may be determined using any known method. Preferably, the methodology described in PCT/US2016/047301 (Soban Balashanmugam et al: Predicting Solvent Power of Light Oils; incorporated herein by reference) is used. This method is generally preferred, particularly for cutter stocks containing asphaltenes in an amount of less than 0.5% by weight (e.g. measured according to IP 143), as it gives the more accurate results.

The reference oil is preferably a heavy oil having an asphaltene content of greater than 3% by weight, and preferably greater than 5% by weight (e.g. measured according to IP 143). The heavy oil will typically have an API gravity of less than 25° (e.g. measured according to ASTM D 4052), and optionally a heavy residue content (i.e. components boiling above 1000° F. (537.8° C.)) of greater than 30% by weight (e.g. measured according to ASTM 5236 of the residue boiling at >300° C. produced from ASTM D 2892 distillation).

According to this method, $SP_{CS}$ is calculated using a method in which the cutter stock is titrated against a reference oil, optionally in the presence of a titrant, to determine a volume fraction of the cutter stock at the onset of asphaltene precipitation, $V_{(onset\ fraction\ CS)}$, a volume fraction of the reference oil at the onset of asphaltene precipitation, $V_{(onset\ fraction\ RO)}$, and, where a titrant is present, a volume fraction of the titrant at the onset of asphaltene precipitation, $V_{(onset\ fraction\ T)}$, and determining $SP_{CS}$ according to the following formula:

$$SP_{CS} = \frac{(CSP_{RO} - SP_{RO} * V_{(onset\ fraction\ RO)}) - x * SP_T * V_{(onset\ fraction\ T)}}{V_{(onset\ fraction\ CS)}}$$

wherein:
$CSP_{RO}$ is the critical solvent power of the reference oil,
$SP_{RO}$ is the solvent power of the reference oil,
$SP_T$ is the solvent power of the titrant, and
x is 1 where a titrant is present, and otherwise is 0.

Any known method may be used to determine the solvent power of the reference oil, $SP_{RO}$, and the solvent power of the titrant, $SP_T$. The solvent power of the titrant, $SP_T$, will generally be known in the art. The solvent power of the reference oil, $SP_{RO}$, (and the solvent power of the titrant, $SP_T$, if not known) may be calculated using the methodology described in US 2004/0121472 (Nemana, S. et al: Predictive Crude Oil Compatibility Model; incorporated herein by reference), according to which solvent power is estimated using the characterisation K factor.

The characterisation K factor, K, for an oil is calculated according to the following formula:

$$K = VABP^{1/3}/SG$$

where:
VABP is the volume average boiling point of the oil, in degrees Rankine, and
SG is the standard specific gravity of the oil.

The volume average boiling point of the oil, VABP, may be determined using known methods. In some instances, VABP may be determined from the yield profile of the oil.

The yield profile oil may be determined from physical distillation, for instance according to ASTM D 2892 or ASTM D 5236. The yield profile of the oil may alternatively be determined using GC and high temperature simulated distillation (HT-SIMDIS). Use of GC analysis allows the hydrocarbon composition of the oil to be determined for components boiling in the $C_{1-9}$ hydrocarbon range. GC analysis may be carried out according to standard test method IP 601. HT-SIMDIS analysis may be carried out according to standard test method IP 545.

The standard specific gravity of the oil, SG, is the ratio of the density of the oil to that of water at 60° F. (i.e. 15.6° C.). SG may be determined using known methods. For instance, the density of the oil may be measured experimentally according to ASTM D 4052 or ASTM D 5002.

The solvent power may be determined from the characterisation K factor using linear interpolation. For instance, SP may be determined from K based on the relationship between the characterisation K factor and the solubility parameter of heptane and toluene.

The characterisation K factor and the solubility parameter of heptane and toluene are known in the art.

The critical solvent power of the reference oil, $CSP_{RO}$, may be determined by titrating the reference oil against a precipitant. In some instances, $CSP_{RO}$ may be determined according to the following formula:

$$CSP_{RO} = V_{(onset\ fraction\ RO(P))} * SP_{RO}/100$$

where:
$V_{(onset\ fraction\ RO(P))}$ is the volume fraction of the reference oil at the onset of asphaltene precipitation with a precipitant; and
$SP_{RO}$ is the solvent power of the reference oil, which may be determined as described above, e.g. based on the characterisation K factor.

The precipitant preferably has a negligible solvent power, such as a solvent power of less than 5, preferably less than 2, and more preferably about 0. Suitable precipitants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the precipitant.

The onset of asphaltene precipitation may be identified by observation of the reference oil and precipitant under an optical microscope, or by other known methods (e.g. gravimetric analysis).

Preferably, asphaltene precipitation is observed on titration of the cutter stock against the reference oil in the absence of a titrant (i.e. x is 0). In these embodiments, the need to conduct experiments with artificial precipitants, such as n-heptane, is advantageously reduced.

However, in some cases, asphaltene precipitation may not be observed on titration of the cutter stock against solely the reference oil. In these cases, the cutter stock may be titrated against the reference oil in the presence of a titrant (i.e. x=1), e.g. a mixture containing the reference oil and the titrant in a ratio of from 2:1 to 1:2, and preferably from 1.5:1 to 1:1.5. Generally, 1:1 mixtures are used. The titrant preferably has a negligible solvent power, such as a solvent power of less than 5, preferably less than 2, and more preferably about 0. Suitable titrants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the titrant.

Alternatively, the solvent power of the cutter stock, $SP_{CS}$, may be determined using the methodology described in US 2004/0121472 (described above), according to which solvent power is estimated using the characterisation K factor. This method has been found to be less accurate for calculating the solvent power of light oils, such as many of the common cutter stocks.

It has surprisingly been found that the correlation between $SP_{CS}$ and the aromatics content of the cutter stock is sufficiently strong to enable $SP_{CS}$ to be determined from the aromatics contents of the cutter stock in the absence of direct measurements of $SP_{CS}$. Accordingly, in some embodiments, $SP_{CS}$ is determined by measuring the aromatics content of the cutter stock, and deriving $SP_{CS}$ using a correlation between aromatics content and $SP_{CS}$.

A correlation between $SP_{CS}$ and the aromatics content of the cutter stock may be determined by measuring the aromatics content and $SP_{CS}$ (e.g. using the method disclosed in PCT/US2016/047301) of a plurality of cutter stocks; and establishing a relationship between the measured aromatics content and the measured $SP_{CS}$.

Aromatics content in cutter stocks may be determined using standard test methods, such as IP 391 or IP 548. These methods are generally preferred for cutter stocks which are not straight run distillates, such as cycle oils and FCC slurry.

The aromatics content of cutter stocks may alternatively be predicted using crude oil assay data. This method is particularly suitable for straight run distillates from CDU and VDU (e.g. naphtha, kerosene, gas oil and vacuum gas oil fractions), since the assays for individual crude oils generally contain measured aromatics content for the various distillate fractions that constitute the full range crude oil. A modelling tool, such as CrudeSuite® (a registered trademark of Spiral Software Limited), may be used to predict the aromatics content of the cutter stock where the straight run distillate is prepared from a mixture of crude oils.

The correlation is preferably determined by measuring the aromatics content and $SP_{CS}$ of at least 10 cutter stocks, more preferably at least 15 cutter stocks, and still more preferably at least 20 cutter stocks. These cutter stocks may be of the same type, i.e. the same refinery stream, or they may be different.

The correlation between aromatics content (expressed in % by weight) and the $SP_{CS}$ of the cutter stocks is preferably expressed as a linear relationship. For instance, the relationship may be expressed using the formula:

$SP_{CS} = X*$aromatics content$+Y$ where X and Y are constants.

Since each refinery is generally supplied with crude oil/cutter stocks from particular sources, then a correlation is preferably determined which is specific to a refinery. In other words, a correlation will preferably be refinery specific.

Moreover, since the profile of the crude oil(s)/cutter stock(s) may vary over time, then the correlation is preferably periodically fine-tuned. Thus, in some embodiments, the correlation is tested and updated at least once a month, preferably at least once a week.

The critical solvent power of the cutter stocks, $CSP_{CS}$, may be assumed to be zero, since they generally contain asphaltenes in negligible amounts.

However, for cutter stocks which contain asphaltenes in an amount of greater than 0.5% by weight (e.g. measured according to IP 143), such as FCC slurry. $CSP_{CS}$ may be predicted using the methodology described in US 2004/0121472 (described above), according to which critical solvent power is estimated using the characterisation K factor. Alternatively, $CSP_{CS}$ may be determined using the titration method described below in connection with the atmospheric residue.

Atmospheric Residue (AR)

Atmospheric residue is the heavier, asphaltene rich fraction of a crude oil. Atmospheric residue is generally defined as having a boiling point (measured under standard atmospheric pressure of 100 kPa) of greater than 300° C. Atmospheric residue is produced from a crude oil atmospheric distillation unit (CDU), and is used as the feed stream to a vacuum distillation unit (VDU). Atmospheric residue may also be used as a feed stream to the visbreaker unit (VSB), together with a vacuum residue feed stream, and as a cutter stock.

The solvent power of the atmospheric residue, $SP_{AR}$, may be determined using any known method. For instance, the methodology described in US 2004/0121472 (described above) may be used. According to this method, solvent power is estimated using the characterisation K factor.

The volume average boiling point of the atmospheric residue, $VABP_{AR}$, may be determined from the yield profile of the crude oil(s) (e.g. determined from physical distillation data, for instance according to ASTM D 2892 or ASTM D 5236) from which the atmospheric residue is derived. A crude oil property modelling tool such as CrudeSuite® (a registered trademark of Spiral Software Limited) may be used to calculate $VABP_{AR}$ from the yield profile.

Alternatively, $SP_{AR}$ may be calculated using a titration method. According to suitable titration methods, the atmospheric residue is titrated against a solvent and a precipitant, to determine a volume fraction of the atmospheric residue at the onset of asphaltene precipitation, $V_{(onset\ fraction\ AR)}$, and a volume fraction of the solvent at the onset of asphaltene precipitation, $V_{(onset\ fraction\ S)}$, and determining $SP_{AR}$ using the following formula:

$$SP_{AR} = \frac{(CSP_{AR} - SP_S * V_{(onset\ fraction\ S)})}{V_{(onset\ fraction\ AR)}}$$

wherein:
$CSP_{AR}$ is the critical solvent power of the atmospheric residue, and
$SP_S$ is the solvent power of the solvent.

The most accurate results are obtained when the precipitant has a negligible solvent power, such as a solvent power of less than 5, preferably less than 2, and more preferably about 0. Suitable precipitants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the precipitant.

The solvent preferably has a solvent power of between 20 and 60. Preferably a solvent is used which has a known solvent power, $SP_S$, though this may also be measured using known methods. Preferred solvents include toluene, xylene and cyclohexane which can be assigned solvent powers of 50, 50 and 30, respectively.

In order to avoid the need to determine $CSP_{AR}$, $SP_{AR}$ is preferably calculated by titrating the precipitant against at least two samples (e.g. 2 to 4 samples) of the atmospheric residue diluted with different amounts of solvent. For instance, 3 samples may be prepared containing 20, 50 and 80% solvent. These methods are similar to that disclosed in ASTM D 7157.

From the formula defining $SP_{AR}$ provided above, it can be seen that $SP_{AR}$ may then be derived from a linear correlation between $SP_S*V_{(onset\ fraction\ S)}$ and $V_{(onset\ fraction\ AR)}$. For example, a graph may be plotted of $SP_S*V_{(onset\ fraction\ S)}$ against $V_{(onset\ fraction\ AR)}$, with the negative of the gradient providing $SP_{AR}$. It will be appreciated that the intercept is equal to $CSP_{AR}$.

Alternatively, the solvent power of an atmospheric residue, $SP_{AR}$, may be predicted merely from its bulk properties. This is because the solvent power of atmospheric residues, e.g. determined using methods mentioned above, may be correlated with the bulk properties of atmospheric residues.

The skilled person would be aware of methods for correlating the solvent powers with the bulk properties of atmospheric residues. Software is readily available for carrying out such methods. Examples include the software program "Nutonian® Eureqa" (a registered trademark of Nutonian, Inc.), though other software packages may be used. In these instances, data on the bulk properties and the solvent power of the atmospheric residues is used as an input, and the software generates a formula linking the solvent power to the bulk properties. Multiple different formulae may be generated, in which case the operator may choose which of the formulae is most useful, e.g. includes bulk properties which are readily or reliably measurable or available.

The correlation is preferably determined based on the bulk properties and solvent power of at least 10 atmospheric residues, more preferably at least 15 atmospheric residues, and still more preferably at least 20 atmospheric residues.

Bulk properties may include: yield, e.g. of the vacuum residue fraction in the atmospheric residue fraction; characterisation K factor, e.g. of the atmospheric residue; nitrogen content, e.g. of the atmospheric residue; and sulfur content, e.g. of the atmospheric residue. Some or all of these properties may be taken into account when determining the relationship between the bulk properties of an atmospheric residue fraction and its solvent power. Other bulk properties may also be used.

The yield of the vacuum residue in the atmospheric residue fraction may be determined by distillation of the residue fraction (typically those components boiling above 300° C.) according to ASTM D 5236. The residue fraction is first generated by distillation of the crude oil according to ASTM D 2892. Preferably, GC SIMDIS analysis (according to IP 545, IP 507 and ASTM D 7169) of the crude oil or fractions obtained using ASTM D 5236 and D 2892 may be used to determine an accurate yield of the vacuum residue.

The characterisation K factor may be calculated using the volume average boiling point (as discussed above) and the density of the atmospheric residue.

The nitrogen content of the atmospheric residue may be measured according to ASTM D 4629, ASTM D5762, IP 379 or equivalent.

The sulfur content of the atmospheric residue may be measured according to ASTM D 4294, or using equivalent X-ray fluorescence spectroscopy methods.

Though the bulk properties of the atmospheric residue may be measured, e.g. as outlined above, they are often readily available from crude oil assay analysis which has been carried out before the crude oil is purchased for use in a refinery. Moreover, in the absence of measured data, a crude oil property modelling tool such as CrudeSuite® (a registered trademark of Spiral Software Limited) may be used to predict properties of the atmospheric residue using limited crude oil property measurements.

The critical solvent power of the atmospheric residue, $CSP_{AR}$, may be assumed to be equal to the critical solvent power of the crude oil (e.g. crude oil blend) from which the atmospheric residue is derived. This assumption is based on the fact that, upon distillation, the asphaltenes in crude oil simply concentrate in the residue fraction and so the critical solvent power is expected to stay constant (provided there is negligible thermal cracking or conversion).

The critical solvent power of a crude oil may be determined using known methods.

In some embodiments, the critical solvent power is determined from the solvent power of the crude oil by titrating the crude oil against a titrant. The following formula may be used:

$$CSP_{crude}=SP_{crude}*(100-CPT_{crude})/100$$

wherein:
$SP_{crude}$ is the solvent power of the crude, and
$CPT_{crude}$ is the critical percentage titrant (vol %) for asphaltene stability in the crude.

In some embodiments, e.g. where the crude oil contains asphaltenes in an amount of less than 0.5% by weight (e.g. measured according to IP 143), the solvent power of the crude oil, $SP_{crude}$, may be predicted using the titration procedure disclosed in PCT/US2016/047301. In other embodiments, e.g. where the crude oil contains asphaltenes in an amount of greater than 0.5% by weight (e.g. measured according to IP 143), solvent power may be predicted using the methodology described in US 2004/0121472 (described above), according to which solvent power is estimated using the characterisation K factor.

The critical percentage titrant (vol %) for asphaltene stability in the crude, $CPT_{crude}$, is the point at which asphaltenes in a mixture of crude and titrant, e.g. n-heptane, become unstable.

$CPT_{crude}$ may be measured directly by titrating the crude oil against the titrant, e.g. following the titration procedure used in PCT/US2016/047301. $CPT_{crude}$ is preferably identified by observing the mixture of crude oil and titrant under an optical microscope, though other methods may also be used (e.g. gravimetric analysis).

The titrant preferably has a negligible solvent power, such as a solvent power of less than 5, preferably less than 2, and more preferably about 0. Suitable titrants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the titrant.

Alternatively, the solvent power and critical solvent power of the crude may be determined using a titration method in which the crude is titrated against a solvent and a precipitant, to determine a volume fraction of the crude at the onset of asphaltene precipitation, $V_{(onset\ fraction\ crude)}$, and a volume fraction of the solvent at the onset of asphaltene precipitation, $V_{(onset\ fraction\ S)}$. The following formula may then be applied:

$$SP_{crude} = \frac{(CSP_{crude} - SP_S * V_{(onset\ fraction\ S)})}{V_{(onset\ fraction\ crude)}}$$

wherein:
$CSP_{crude}$ is the critical solvent power of the crude oil, and
$SP_S$ is the solvent power of the solvent.

The most accurate results are obtained when the precipitant has a negligible solvent power, such as a solvent power of less than 5, preferably less than 2, and more preferably about 0. Suitable precipitants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the precipitant.

The solvent preferably has a solvent power of between 20 and 60. Preferably a solvent is used which has a known solvent power, $SP_S$, though this may also be measured using known methods. Preferred solvents include toluene, xylene and cyclohexane which can be assigned solvent powers of 50, 50 and 30, respectively.

In order to avoid the need to determine $CSP_{crude}$ or $SP_{crude}$, the precipitant may be titrated against at least two samples (e.g. 2 to 4 samples) of the crude oil diluted with different amounts of solvent. For instance, 3 samples may be prepared containing 20, 50 and 80% solvent. These methods are similar to that disclosed in ASTM D 7157.

From the formula provided above, it can be seen that $SP_{crude}$ may then be derived from a linear correlation between $SP_S * V_{(onset\ fraction\ S)}$ and $V_{(onset\ fraction\ crude)}$. For example, a graph may be plotted of $SP_S * V_{(onset\ fraction\ S)}$ against $V_{(onset\ fraction\ crude)}$, with the negative of the gradient providing $SP_{crude}$ and the intercept providing $CSP_{crude}$.

Where the atmospheric residue is derived from a blend of n crude oils residues, $CSP_{AR}$ may be calculated based on the following formula:

$$CSP_{AR} = \sum_{i=1}^{n} \frac{(Wt\ \%_i * Asp\ content_i)}{Asp\ content_{(blend\ AR)}} * CSP_i$$

wherein:
Wt $\%_i$ is the %, by weight, of each of the n crude oil residues
Asp content$_i$ is the asphaltene content of each of the n crude oil residues,
Asp content$_{(blend\ AR)}$ is the asphaltene content of the atmospheric residue blend, and
$CSP_i$ is the critical solvent power of each of the n crude oil residues.

Asphaltene content may be measured using known methods, e.g. according to IP 143. Asphaltene content may be measured on the crude oil itself, or on residues of the crude oil during the crude oil assay process. Since asphaltene content is a property that mass balances, the yield profile of the crude oil and the asphaltene content of the crude oil, residues or both may be used to calculate the asphaltene content in a particular residue or the whole crude oil.

The critical solvent power of each of the crude oil residues may be determined using the methods outlined above.

Vacuum Residue (VR)

Vacuum residue is the heaviest, asphaltene rich fraction of a crude oil. Vacuum residue is generally defined as having a boiling point (measured under standard atmospheric pressure of 100 kPa) of greater than 500° C. Typically, vacuum residue is produced in a vacuum distillation unit (VDU) for which atmospheric residue is the feedstock. Vacuum residue is used as the principle feed stream to the visbreaker unit (VSB). Vacuum residue may also occasionally be blended into fuel oil.

The solvent power of a vacuum residue, $SP_{VR}$, may be determined using the following equation:

$$SP_{VR} = 100 * CSP_{VR}/(100 - CPT_{VR})$$

wherein:
$CSP_{VR}$ is the critical solvent power of the vacuum residue, and
$CPT_{VR}$ is the critical percentage titrant (vol %) for asphaltene stability in the vacuum residue.

The critical solvent power of the vacuum residue, $CSP_{VR}$, may be assumed to be equal to the critical solvent power of the crude oil(s) from which the vacuum residue is derived. As discussed previously, this may also be assumed to be equal to the critical solvent power of the atmospheric residue, $CSP_{AR}$.

The critical percentage titrant (vol %) for asphaltene stability in the vacuum residue, $CPT_{VR}$, is the point at which asphaltenes in a mixture of vacuum residue and titrant, e.g. n-heptane, become unstable.

$CPT_{VR}$ may be measured directly by titrating the vacuum residue against the titrant, e.g. following the titration procedure used in PCT/US2016/047301. $CPT_{VR}$ is preferably identified by observing the mixture of vacuum residue and titrant under an optical microscope, though other methods may also be used (e.g. gravimetric analysis).

The titrant preferably has a negligible solvent power, such as a solvent power of less than 5, preferably less than 2, and more preferably about 0. Suitable titrants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the titrant.

Where difficulty is encountered with mixing the heavy vacuum residue with the titrant, the residue and titrant may be heated, e.g. to a temperature in the range of from 40 to 100° C., and/or sonicated, e.g. for up to 15 minutes. In the case of extremely viscous residues, temperatures in the range of from 80 to 100° C. may be adopted. The use of higher carbon number paraffins (e.g. $C_{10-20}$) as the titrant may also aid mixing of vacuum residues with the titrant.

Alternatively, $CPT_{VR}$ may be predicted from the critical percentage titrant (vol %) for asphaltene stability in an atmospheric residue, $CPT_{AR}$, the atmospheric residue stream being derived from the same crude oil(s) as the vacuum residue, using a correlation between $CPT_{VR}$ and $CPT_{AR}$.

The correlation may be obtained by a method which comprises, for each of a plurality of crude oils, measuring $CPT_{VR}$ of a vacuum residue stream derived from the crude oil and $CPT_{AR}$ of an atmospheric residue stream derived from the crude oil, and determining a correlation between $CPT_{VR}$ and $CPT_{AR}$. In some embodiments, the method for predicting $CPT_{VR}$ may comprise obtaining the correlation, and then using the correlation to predict $CPT_{VR}$.

The atmospheric residue and vacuum residue streams are derived from the same crude oil. In preferred embodiments, the streams are produced in a refinery process in which the atmospheric residue stream is produced from crude oil in a CDU and is used as the feed stream to a VDU, and the vacuum residue stream is produced in the VDU. $CPT_{AR}$ may be measured, e.g. using the methods disclosed in connection with $CPT_{VR}$. However, $CPT_{AR}$ is preferably determined using the following formula:

$$CPT_{AR}=100-(100*CSP_{AR})/SP_{AR}$$

wherein:
$CSP_{AR}$ is the critical solvent power of the atmospheric residue, e.g. determined using the methods disclosed herein, and
$SP_{AR}$ is the solvent power of the atmospheric residue.
Methods for determining $CSP_{AR}$ and $SP_{AR}$ are provided above.

A correlation between $CPT_{VR}$ and $CPT_{AR}$ may be determined by measuring the critical percentage titrant (vol %) of a plurality of atmospheric residues and vacuum residues derived from the same crude oil(s) (e.g. using the methods described above in connection with $CPT_{VR}$) and establishing a relationship between the measured $CPT_{VR}$ and $CPT_{AR}$.

The correlation is preferably determined by measuring the $CPT_{VR}$ and $CPT_{AR}$ of residues derived from at least 10 crude oils, more preferably at least 15 crude oils, and still more preferably at least 20 crude oils.

The correlation between $CPT_{VR}$ and $CPT_{AR}$ is preferably expressed as a linear relationship.

Visbroken Residue (VisRes)

Visbroken residue streams are produced in a visbreaker unit (VSB). The feed to a VSB typically consists of 100% vacuum residue, though atmospheric residue may also be passed to the VSB in an amount of from 0-15% by volume of the total feed.

Visbreaking is preferably carried out at a temperature in the range of from 400 to 500° C., and more preferably in the range of from 420 to 490° C. The VSB may be a coil-type visbreaker (where the reactions occur within a few seconds in the tubes of the furnace), or a soaker-drum type unit (where the reactions occur within a few minutes largely in a soaker drum). Since soaker-drum type VSBs are operated at a slightly lower temperature than coil-type VSBs, they exhibit a lower propensity for furnace tube coking and so are preferred.

The solvent power of the visbroken residue, $SP_{VisRes}$, and the critical solvent power of the visbroken residue, $CSP_{VisRes}$, may be determined using the methods described above in connection with the atmospheric residue, and more preferably the titration and linear correlation method. According to this method, a graph may be plotted of $SP_S*V_{(onset\ fraction\ S)}$ against $V_{(onset\ fraction\ VisRes)}$, with the negative of the gradient providing $SP_{VisRes}$ and the intercept providing $CSP_{VisRes}$.

However, it has surprisingly been found that a correlation exists between $CSP_{VisRes}$ and the critical percentage titrant (vol %) in an atmospheric residue stream, $CPT_{AR}$, the atmospheric residue stream being derived from the same crude oil as the visbroken residue stream, which may be used to determine $CSP_{VisRes}$ from $CPT_{AR}$. This means that the visbroken stream does not need to be analysed to determine its critical solvent power.

Thus, a method for predicting the critical solvent power of a visbroken residue stream of interest, $CSP_{VisRes(OI)}$ comprises predicting $CSP_{VisRes(OI)}$ from the critical percentage titrant (vol %) for asphaltene stability of an atmospheric residue stream, $CPT_{AR}$, the atmospheric residue stream being derived from the same crude oil as the visbroken residue stream, using a correlation between the critical solvent power of a visbroken residue stream, $CSP_{VisRes}$, and the critical percentage titrant (vol %) for asphaltene stability in an atmospheric residue stream, $CPT_{AR}$. In some embodiments, the method may further comprise determining the critical percentage titrant (vol %) of the atmospheric residue stream $CPT_{AR}$.

The correlation has been obtained by a method which comprises, for each of a plurality of crude oils, measuring $CSP_{VisRes}$ of a visbroken residue stream derived from the crude oil and $CPT_{AR}$ of an atmospheric residue stream derived from the crude oil, and determining a correlation between $CSP_{VisRes}$ and $CPT_{AR}$. In some embodiments, the method for predicting $CSP_{VisRes}$ may comprise obtaining the correlation, and then using the correlation to predict $CSP_{VisRes(OI)}$ for a visbroken residue stream of interest.

The critical percentage titrant (vol %) for asphaltene stability in an atmospheric residue stream, $CPT_{AR}$, is the point at which asphaltenes in a mixture of atmospheric residue and titrant, e.g. n-heptane, become unstable. It will be appreciated that the following methods may be used to determine both $CPT_{AR}$ for the purposes of obtaining the correlation and $CPT_{AR}$ for the purposes of predicting the critical solvent power of the visbroken residue stream of interest.

$CPT_{AR}$ may be determined by direct measurement by titrating the atmospheric residue against the titrant, e.g. following the titration procedure used in PCT/US2016/047301. $CPT_{AR}$ is preferably identified by observing the mixture of atmospheric residue and titrant under an optical microscope, though other methods may also be used (e.g. gravimetric analysis).

The titrant preferably has a negligible solvent power, such as a solvent power of less than 5, preferably less than 2, and more preferably about 0. Suitable titrants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the titrant. In this case, a correlation exists between $CSP_{VisRes}$ and the critical percentage heptane (vol %) for asphaltene stability in an atmospheric residue stream, $CPH_{AR}$.

However, $CPT_{AR}$ is preferably predicted using the following formula:

$$CPT_{AR}=100-(100*CSP_{AR})/SP_{AR}$$

wherein:
$CSP_{AR}$ is the critical solvent power of the atmospheric residue, and
$SP_{AR}$ is the solvent power of the atmospheric residue.
Methods for determining $CSP_{AR}$ and $SP_{AR}$ are provided herein.

The correlation is preferably determined by measuring $CPT_{AR}$ and $CSP_{VisRes}$ of streams derived from at least 10 crude oils, more preferably at least 15 crude oils, and still more preferably at least 20 crude oils.

The correlation between $CPT_{AR}$ and $CSP_{VisRes}$ is preferably expressed as a linear relationship.

The atmospheric residue and visbroken residue streams are derived from the same crude oil (e.g. crude oil blend). In preferred embodiments, the streams are produced in a refinery process in which the atmospheric residue stream is produced from crude oil in a CDU and is used as the feed stream to a VDU, and a vacuum residue stream is produced in the VDU and is used as the feed stream to a VSB in which the visbroken residue is produced.

Preferably, the method for obtaining a correlation between $CPT_{AR}$ and $CSP_{VisRes}$ comprises: assigning each of the plurality of crude oils to a subgroup based on the ratio of the feed rate to coil outlet temperature (COT) of the VSB in which the visbroken residue is produced, and determining a relationship between $CPT_{AR}$ and $CSP_{VisRes}$ for each subgroup. By taking into account the ratio of feed rate to COT, the correlation between $CPT_{AR}$ and $CSP_{VisRes}$ is enhanced. In these embodiments, the method for predicting $CSP_{VisRes(OI)}$ comprises predicting $CSP_{VisRes(OI)}$ from the critical percentage titrant (vol %) for asphaltene stability in an atmospheric residue stream, $CPT_{AR}$, derived from the same crude oil as the visbroken residue stream, and the ratio of feed rate to COT of the VSB in which the visbroken residue of interest is produced.

As the skilled person is aware, the COT represents the bulk temperature of the feed at the outlet of the VSB, and the feed rate represents the rate at which the feed streams are passed to the VSB. In some embodiments, the method for obtaining a correlation between $CPT_{AR}$ and $CSP_{VisRes}$ may comprise measuring the feed rate and coil outlet temperature (COT) of the VSB. Methods for measuring COT and feed rate are well known in the art. Frequent monitoring of COT and feed rate, as well as $CPT_{AR}$, in a refinery enables the correlation to be fine-tuned.

The solvent power of the visbroken residue stream, $SP_{VisRes}$, is a complex function of feed properties and operating conditions. Given the diversity and complexity of molecules in VSB feed, predicting an accurate change in composition of feed (in terms of molecular changes and resulting impact on SP) is an extremely complex challenge.

However, according to the present invention, the solvent power of the visbroken residue stream, $SP_{VisRes}$, may be determined using the following formula:

$$SP_{VisRes} = (100 \times CSP_{VisRes})/(100 - CPT_{VisRes})$$

wherein:
$CSP_{VisRes}$ is the critical solvent power of the visbroken residue, e.g. determined as outlined above; and
$CPT_{VisRes}$ is the critical percentage titrant (vol %) for asphaltene stability in the visbroken residue stream.

The critical percentage titrant (vol %) for asphaltene stability in the visbroken residue stream, $CPT_{VisRes}$, is the point at which asphaltenes in a mixture of atmospheric residue and titrant, e.g. n-heptane, become unstable.

$CPT_{VisRes}$ may be measured directly by titrating the visbroken residue against the titrant, e.g. following the titration procedure used in PCT/US2016/047301. $CPT_{VisRes}$ is preferably identified by observing the mixture of visbroken residue and titrant under an optical microscope, though other methods may also be used (e.g. gravimetric analysis).

The titrant preferably has a negligible solvent power, such as a solvent power of less than 5, preferably less than 2, and more preferably about 0, since titrants having smaller solvent power values give more accurate results. Suitable titrants include alkanes, such as $C_{5-20}$ alkanes, preferably $C_{5-20}$ n-alkanes or $C_{5-20}$ iso alkanes, and more preferably $C_{5-8}$ n-alkanes or $C_{5-8}$ iso alkanes. Preferably, n-heptane is used as the titrant. In this case, a correlation exists between $CSP_{VisRes}$ and the critical percentage heptane (vol %) for asphaltene stability in an atmospheric residue stream, $CPH_{AR}$.

However, $CPT_{VisRes}$ is preferably estimated from the P-value of the visbroken residue stream.

VSB units are operated such that a target P-value is achieved in the visbroken residue stream that is produced. Typical target P-values for a visbroken residue stream produced by a VSB is in the range of from 1.10 to 1.30. P-value is frequently monitored in a refinery (e.g. 2 to 3 times per day, or more frequently when crude slate changes are made), so this data is readily available in order to estimate $CPT_{VisRes}$ using the method outlined below.

The P-value of a visbroken residue stream is defined according to standard test method SMS 1600-01 using the following formula:

$$P\text{-value} = 1 + X_{min}$$

wherein:
$X_m$ in is the quantity of cetane with which one gram of visbroken residue stream may be diluted before asphaltene flocculation occurs (ml/g)

However, P-value can also be expressed in terms of the critical percentage cetane (vol %) for asphaltene stability in the visbroken residue stream, $CPC_{VisRes}$, i.e. the point at which asphaltenes in a mixture of visbroken residue stream and cetane become unstable. The following formula relates $CPC_{VisRes}$ to P-value:

$$CPC_{VisRes} = ([(P\text{-value}-1) * \rho_{VisRes}]/[((P\text{-value}-1) * \rho_{VisRes})+1]) * 100$$

wherein:
$\rho_{VisRes}$ is the density of the visbroken residue stream.

Density of the visbroken residue stream may be determined using known methods, e.g. according to ASTM D 4052. Preferably, density is determined at a temperature in the range of from 80 to 100° C.

Thus, once the density and P-value of the visbroken residue stream are known, $CPT_{VisRes}$ may be derived from $CPC_{VisRes}$ using the following formula:

$$CPT_{VisRes} = CF + CPC_{VisRes}$$

wherein:
CF is a conversion factor that relates $CPT_{VisRes}$ to $CPC_{VisRes}$.

It will be understood that, where the titrant is cetane (i.e. hexadecane), then CF will be equal to zero. However, in some instances, it is preferable to measure asphaltene stability in the visbroken residue stream using a titrant other than cetane, e.g. using an alkane having a shorter chain length than cetane such as heptane.

The conversion factor, CF, may be determined using a method which comprises measuring $CPT_{VisRes}$ and $CPC_{VisRes}$ for a plurality of visbroken residue streams; and establishing a relationship between the measured $CPT_{VisRes}$ and the measured $CPC_{VisRes}$. The relationship will generally be a linear relationship, and CF a constant.

The correlation is preferably determined by measuring the $CPT_{VisRes}$ and $CPC_{VisRes}$ of at least 10 visbroken residue streams, more preferably at least 15 visbroken residue streams, and still more preferably at least 20 visbroken residue streams.

Fuel Oil

Fuel oil is a blend of the visbroken residue stream with one or more blend components, such as cutter stocks. Atmospheric residue and vacuum residue streams may also be used as blend components in the fuel oil.

The solvent power of the fuel oil containing n blend components, $SP_{FO}$, may be predicted using the following formula:

$$SP_{FO} = \sum_{i=1}^{n} Vol\, \%_i * SP_i$$

wherein:
Vol $\%_i$ is the % by volume of each of the n blend components in the fuel oil, and $SP_i$ is the solvent power of each of the n blend components.

The % by volume of each of the n blend components is a standard parameter that is measurable and controllable by a refinery operator.

$SP_i$ may be determined for the visbroken residue stream and the cutter stocks using the methods described herein.

The critical solvent power of the fuel oil containing n blend components, $CSP_{FO}$, may be predicted using the following formula:

$$CSP_{FO} = \sum_{i=1}^{n} \frac{(\text{Wt \%}_i * Asp\ content_i)}{Asp\ content_{(FO)}} * CSP_i$$

wherein:
Wt %$_i$ is the %, by weight, of each of the n blend components

Asp content$_i$ is the asphaltene content of each of the n blend components,

Asp content$_{(FO)}$ is the asphaltene content of the fuel oil, and $CSP_i$ is the critical solvent power of each of the n blend components oils.

Asphaltene content may be measured using known methods, e.g. according to IP 143.

The critical solvent power of each of the blend components may be determined using methods disclosed herein.

Visbroken Residue and Fuel Oil Stability

Once the solvent power of the visbroken residue stream, $SP_{VisRes}$, and the critical solvent power of the visbroken residue stream, $CSP_{VisRes}$, have been established, then the stability of the visbroken residue stream may be predicted. In order for the asphaltenes in the visbroken residue stream to be stable, then $SP_{VisRes}$ must be greater than $CSP_{VisRes}$. Accordingly, the present invention provides a method for assessing the stability of a visbroken residue stream in which $SP_{VisRes}$ is compared with $CSP_{VisRes}$ and, if $SP_{VisRes}$ is larger than $CSP_{VisRes}$, categorising the visbroken residue stream as stable. In some embodiments, the visbroken residue stream is categorised as stable if $SP_{VisRes}$ is at least 10%, and more preferably 15% larger than $CSP_{VisRes}$.

Similarly, in order for the asphaltenes in the fuel oil to be stable, then the solvent power of the fuel oil, $SP_{FO}$, must be greater than the critical solvent power of the fuel oil, $CSP_{FO}$. Accordingly, the present invention provides a method for assessing the stability of a fuel oil in which $SP_{FO}$ is compared with $CSP_{RO}$ and, if $SP_{FO}$ is larger than $CSP_{RO}$, categorising the fuel oil as stable. In some embodiments, the fuel oil is categorised as stable if $SP_{FO}$ is at least 25%, and more preferably 33% larger than $CSP_{FO}$.

It is preferably also the case that the P-value of the fuel oil is at least 1.05, and preferably at least 1.10. Assuming a fuel oil density of 1, critical percentage cetane (vol %) for asphaltene stability in the fuel oil, $CPC_{FO}$, must be at least 5%, and preferably at least 9%.

However, as outlined above in connection with the visbroken residue stream, it may be preferable, e.g. more accurate, to measure asphaltene stability in the fuel oil stream using a titrant other than cetane, e.g. a titrant which is a $C_{5-8}$ n-alkane or $C_{5-8}$ iso alkane. Preferably, n-heptane is used as the titrant. Thus, for the fuel oil to be categorised as stable, it will preferably have a critical percentage titrant (vol %) for asphaltene stability in the fuel oil, $CPT_{FO}$, which satisfies the following formula:

$$CPT_{FO} > CF + CPC_{FO}$$

wherein:
CF is a conversion factor that relates $CPT_{RO}$ to $CPC_{FO}$, and $CPC_{RO}$ is at least 5% and preferably at least 9%.

It will be understood that, where the titrant is cetane (i.e. hexadecane), then CF will be equal to zero.

The conversion factor, CF, may be determined using a method which comprises measuring $CPT_{FO}$ and $CPC_{Ro}$ for a plurality of fuel oils; and establishing a relationship between the measured $CPT_{FO}$ and the measured $CPC_{FO}$. The relationship will generally be a linear relationship, and CF a constant.

The correlation is preferably determined by measuring the $CPT_{FO}$ and $CPC_{FO}$ of at least 10 fuel oil streams, more preferably at least 15 fuel oil streams, and still more preferably at least 20 fuel oil streams.

The conversion factor, CF, may also be determined in an analogous manner by critical percentage titrant (vol %) and critical percentage cetane (vol %) measurements taken on the visbroken residue stream, since this is the main component of the fuel oil.

Where the visbroken residue or the fuel oil is not categorized as stable, then adjustments may be made to the refinery process to bring the visbroken residue or fuel oil into line with the stability requirements. Thus, the present invention further provides a method for preventing the precipitation of asphaltenes from a visbroken residue (e.g. in the VSB, such as in the furnace tubes or soaker drum) or a fuel oil, said method comprising predicting the stability of the visbroken residue or a fuel oil using a method disclosed herein and, where the visbroken residue or fuel oil is categorised unstable, adjusting the refinery process to ensure that the visbroken residue or fuel oil meets the stability requirements.

The skilled person would be aware of methods for adjusting the refinery process, such as modifying the feed to, or conditions in, the VSB, or adjusting the amount or type of cutter stocks that are added to the visbroken residue stream to form the fuel oil.

It will be appreciated that the methods disclosed herein may be carried out using measurements taken from on a full-scale refinery, or they may be carried out on a laboratory scale in order to predict the outcome of a full-scale refinery operation. In this regard, the equations disclosed herein may form part of predictive algorithms, and can be implemented in scheduling tools such as "Orion", provided by AspenTech, in order to assess forward plans for fuel oil blending. This enables refiners to assess the risk of fuel oil instability weeks if not months in advance, based on planned crude slates, throughput and other factors. Unstable or high risk fuel oil blends can be identified in advance, allowing the refiner to make changes to the blend or VSB operation and/or schedule lab test batches to be prepared in advance for further confirmation of predictions. The fuel oil blending procedure can be further optimized to reduce give-away of valuable components, e.g. atmospheric residue, whilst ensuring that the fuel oil product meets asphaltene stability specifications.

The invention will now be described with reference to the accompanying non-limiting examples.

EXAMPLES

Example 1: Predicting the Solvent Power and Critical Solvent Power of a Cutter Stock The solvent power of a series of 36 cutter stocks, $SP_{CS}$, was measured using the titration method disclosed in PCT/US2016/047301. Analytical measurements were also carried out on the cutter stocks. A strong correlation between $SP_{CS}$ and the aromatics content of the cutter stocks was observed.

A graph showing the correlation between $SP_{CS}$ and the aromatics content of the cutter stocks is shown in FIG. 1. The correlation was found to be sufficiently strong to enable $SP_{CS}$ to be determined from the aromatics contents of the cutter stock in the absence of direct measurements of $SP_{CS}$.

The critical solvent power, of the cutter stocks, $CSP_{CS}$, was assumed to be equal to zero.

Example 2: Predicting the Solvent Power and Critical Solvent Power of an Atmospheric Residue The solvent power of a series of 43 atmospheric residue samples, $SP_{AR}$, was measured using the titration method described herein as similar to that disclosed in ASTM D 7157. Toluene, xylene and cyclohexane were used as solvents. $SP_{AR}$ was derived from a graph of $SP_S * V_{(onset\ fraction\ S)}$ against $V_{(onset\ fraction\ AR)}$, with the negative of the gradient providing $SP_{AR}$. The following correlation between $SP_{AR}$ and the bulk properties of the atmospheric residue samples was obtained by non-linear regression using the software program "Nutonian® Eureqa" (a registered trademark of Nutonian, Inc.):

$$SP_{AR} = 570.7 * WTK + 1.1 * \text{yield vacuum residue (wt \%)} +$$
$$0.0025 * \text{nitrogen content (ppm)} + 0.67 * [\text{sulfur content (wt \%)}]^2 -$$
$$3174.7 - 0.00072 * \text{sulfur content (wt \%)} * \text{nitrogen content (wt \%)} -$$
$$0.011 * [\text{yield vacuum residue (wt \%)}]^2 - 25.5 * [WTK]^2$$

Figure 2:
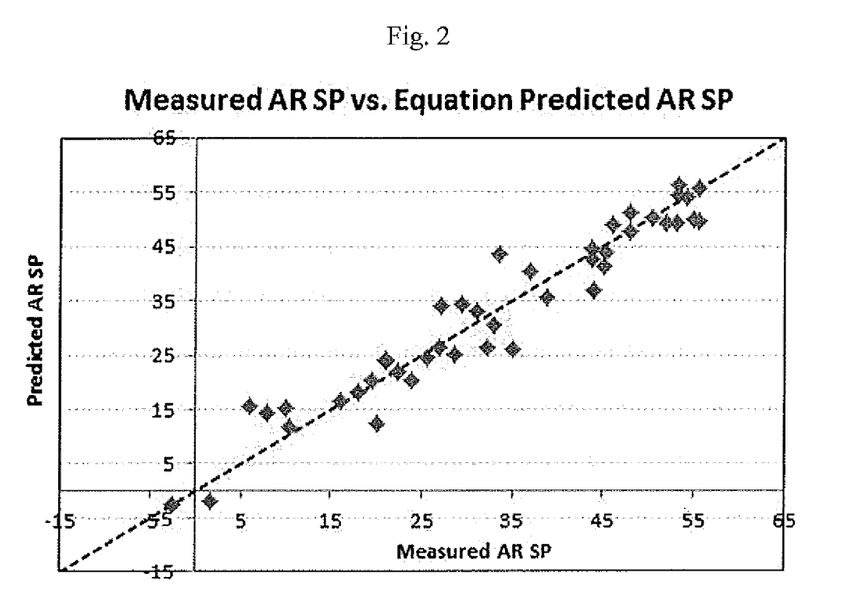
FIG. 2 is a graph comparing the solvent power of aromatic residues, $SP_{AR}$, as measured and as predicted from their bulk properties using a method of the present invention.

The correlation was found to be sufficiently strong to enable $SP_{AR}$ to be predicted from its bulk properties. A graph comparing predicted and measured $SP_{AR}$ is shown in FIG. 2, and demonstrates the accuracy of the method for predicting $SP_{AR}$ from its bulk properties.

The critical solvent power of the atmospheric residue streams, $CSP_{AR}$, was assumed to be equal to the critical solvent power of the crude oils from which the atmospheric residue streams were derived.

Example 3: Predicting the Solvent Power and Critical Solvent Power of a Vacuum Residue The critical percentage heptane of a series of 22 pairs of atmospheric residue samples from a CDU, $CPH_{AR}$, and vacuum residue samples from a VDU, $CPH_{VR}$, was measured using the titration method disclosed in PCT/US2016/047301. To overcome difficulty in mixing the heavier vacuum residues with the heptane titrant, mixtures of the sample and titrant were heated to a temperature of from 40 to 100° C. and sonicated for up to 15 minutes. A correlation between $CPH_{AR}$ and $CPH_{VR}$ was observed.

Figure 3:
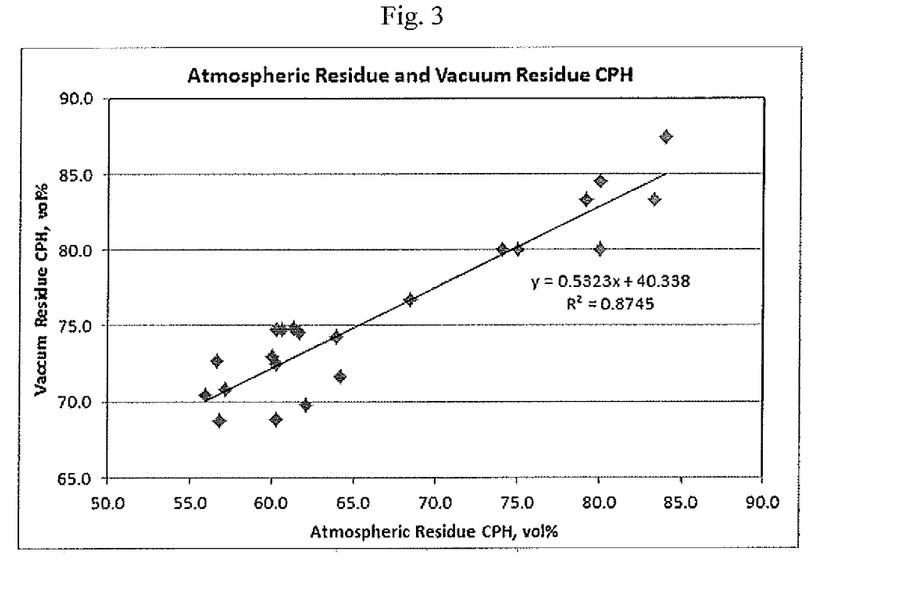
FIG. 3 is a graph showing the correlation between the critical percentage heptane of aromatic residues, $CPH_{AR}$, and the critical percentage heptane of vacuum residues, $CPH_{VR}$.

A graph showing the correlation between $CPH_{AR}$ and $CPH_{VR}$ is shown in FIG. 3. The correlation was found to be sufficiently strong to enable $CPH_{VR}$ to be predicted from $CPH_{AR}$.

The solvent power of a vacuum residue, $SP_{VR}$, was then determined using the following equation:

$$SP_{VR} = 100 * CSP_{VR}/(100 - CPH_{VR})$$

wherein:
$CSP_{VR}$ is the critical solvent power of the vacuum residue, and
$CPH_{VR}$ is the critical percentage heptane (vol %) for asphaltene stability in the vacuum residue, predicted from $CPH_{AR}$.

It was believed that the critical solvent power of the vacuum residue, $CSP_{VR}$, (as with the critical solvent power of the atmospheric residue, $CSP_{AR}$) could be assumed to be equal to the critical solvent power of the crude oil(s) from which the vacuum residue is derived. However, since some thermal cracking can occur across a VDU, this assumption was tested by direct measurements of $CSP_{VR}$ and $CSP_{AR}$.

Figure 4:
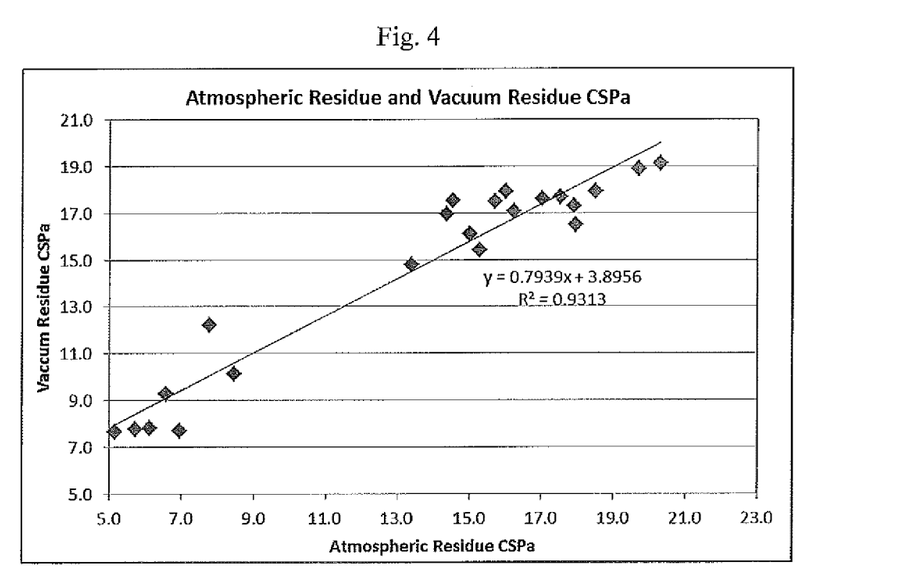
FIG. 4 is a graph showing the relationship between the critical solvent power of vacuum residues, $CSP_{VR}$, and the critical solvent power of aromatic residues, $CSP_{AR}$.

A graph showing the relationship between $CSP_{VR}$ and $CSP_{AR}$ is shown in FIG. 4. It can be seen that $CSP_{VR}$ and $CSP_{AR}$ are very similar for the streams derived from each crude oil. The assumption that $CSP_{VR}$ is equal to the critical solvent power of the crude oil from which it was derived was therefore followed.

Example 4: Predicting the Solvent Power and Critical Solvent Power of a Visbroken Residue The solvent power, $SP_{VisRes}$, and critical solvent power, $CSP_{VisRes}$, of a series of 22 visbroken residue samples (generated from the 22 pairs of atmospheric residue and vacuum residue streams of Example 3) were measured using the titration method described herein as similar to that disclosed in ASTM D 7157. $SP_{VisRes}$ was derived from a graph of $SP_S * V_{(onset\ fraction\ S)}$ against $V_{(onset\ fraction\ VisRes)}$, with the negative of the gradient providing $SP_{VisRes}$ and the intercept providing $CSP_{VisRes}$.

Figure 5A:
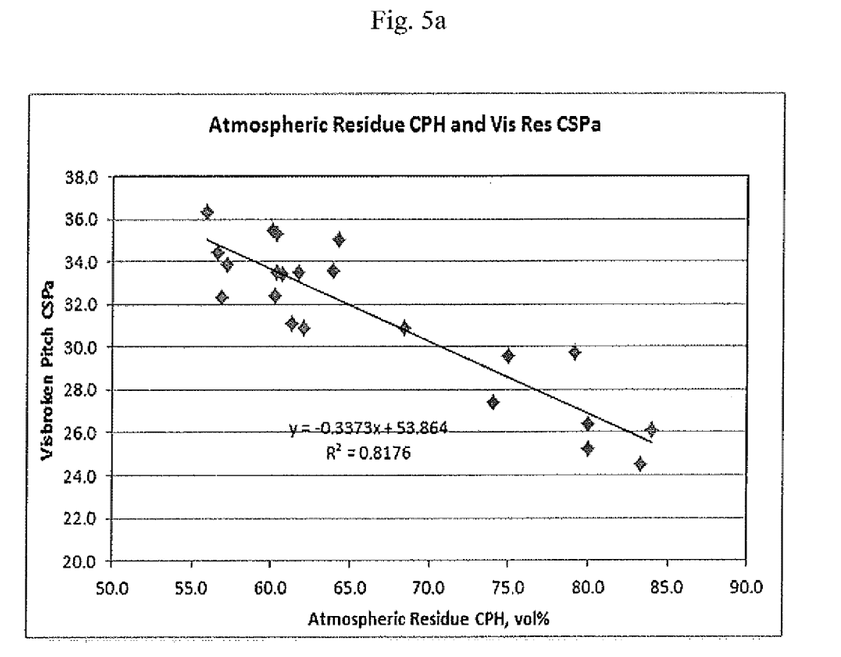
FIG. 5a is a graph showing the correlation between the critical solvent power of visbroken residue streams, $CSP_{VisRes}$, and the critical percentage heptane in the corresponding atmospheric residue stream, $CPH_{AR}$.

A correlation between $CSP_{VisRes}$ and the critical percentage heptane for asphaltene stability (vol %) in the corresponding atmospheric residue stream, $CPH_{AR}$, was observed. A graph showing the correlation is shown in FIG. 5a. The correlation was found to be sufficiently strong to enable $CSP_{VisRes}$ to be determined from $CPH_{AR}$.

Figure 5B:
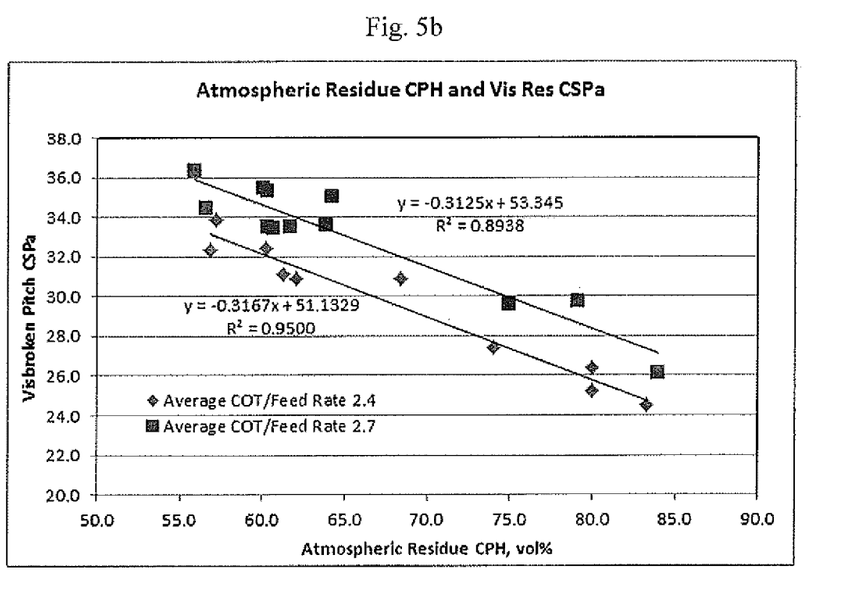
FIG. 5b is a graph showing the relationship shown in FIG. 5a but in which the ratios of feed rate to coil outlet temperature (COT) of the VSB in which the visbroken residues were produced have been taken into account.

However, it was noticed that, by taking into account the ratio of feed rate to coil outlet temperature (COT) of the VSB in which the visbroken residue was produced, the correlation between $CPH_{AR}$ and $CSP_{VisRes}$ was greatly enhanced. The improved correlations are shown in FIG. 5b.

To enable the solvent power of the visbroken residue, $SP_{VisRes}$, to predicted from the target P-value of the VSB in which the visbroken residue stream was produced, a conversion factor, CF, was first determined that relates the critical percentage heptane (vol %) for asphaltene stability in the visbroken residue stream, $CPH_{VisRes}$, to the critical percentage cetane (vol %) for asphaltene stability in the visbroken residue stream, $CPC_{VisRes}$. Measurements obtained on atmospheric residue streams were also included when determining the relationship.

Figure 5C:
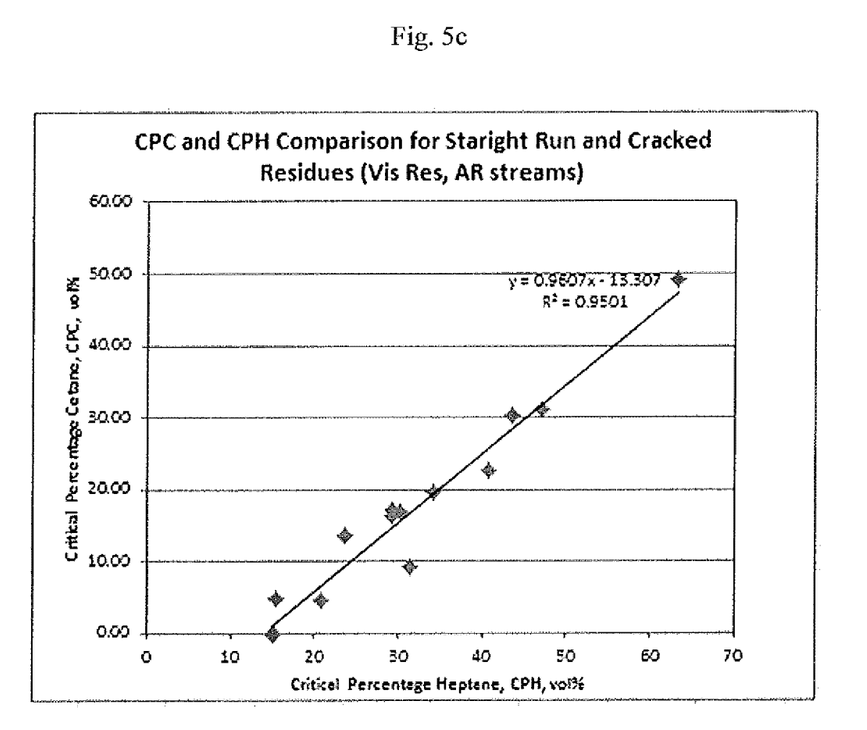
FIG. 5c is a graph showing the relationship between the critical percentage heptane, $CPH_{VisRes}$, and the critical percentage cetane, $CPC_{VisRes}$, in visbroken residue streams.

A graph showing the relationship between $CPH_{VisRes}$ and $CPC_{VisRes}$ is shown in FIG. 5c. The correlation was found to be sufficiently strong to enable $CPH_{VisRes}$ to be determined from $CPC_{VisRes}$, and thus the target P-value.

$SP_{VisRes}$ was then determined using the following formula:

$$SP_{VisRes} = (100 \times CSP_{VisRes})/(100 - CPT_{VisRes})$$

Example 5: Predicting the Stability of Fuel Oils

The stability of three different fuel oil blends was predicted using the solvent power and critical solvent powers determined in Examples 1 to 4. The target P-value was taken as 1.10, and the density of the fuel oils assumed to be 1.00. The results are shown in the following table:

|  | Vol. % | Density @ 20° C., g/cc | wt % | SP | CSPa | Asphaltenes, wt % |
|---|---|---|---|---|---|---|
| Components, Fuel Oil Blend 1 | | | | | | |
| Vis Res-1 | 67 | 1.0131 | 69 | 53 | 36 | 9.6 |
| AR-1 | 23 | 0.9523 | 22 | 35 | 14 | 2.1 |
| Gas Oil Cutter-1 | 10 | 0.8518 | 9 | 12 | 0 | 0 |
| Blend SP | 44.8 | | | | | |
| Blend CSPa | 34.5 | | | | | |
| Blend Asphaltenes, wt % | 7.1 | | | | | |
| CPH | 22.8 | | | | | |
| Components, Fuel Oil Blend 2 | | | | | | |
| Vis Res-2 | 80 | 1.0098 | 81 | 48 | 29 | 10.2 |
| AR-2 | 5 | 0.9502 | 5 | 29 | 12 | 1.7 |
| Gas Oil Cutter-2 | 15 | 0.9422 | 14 | 45 | 0 | 0 |
| Blend SP | 46.6 | | | | | |
| Blend CSPa | 28.8 | | | | | |
| Blend Asphaltenes, wt % | 8.3 | | | | | |
| CPH | 38.1 | | | | | |
| Components, Fuel Oil Blend 3 | | | | | | |
| Vis Res-3 | 68 | 1.0065 | 70 | 48 | 36 | 9.6 |
| AR-3 | 10 | 1.0355 | 11 | 65 | 50 | 0.8 |
| Gas Oil Cutter-3 | 22 | 0.8566 | 19 | 12 | 0 | 0 |
| Blend SP | 41.8 | | | | | |
| Blend CSPa | 36.2 | | | | | |
| Blend Asphaltenes, wt % | 6.8 | | | | | |
| CPH | 13.4 | | | | | |

Notes for Blend 1: Blend CPH ~23. Borderline stability. Recommend adjusting blend components or checking test batch for P-value/aged sediments in lab first.

Notes for Blend 2: Blend CPH ~38. Good stability. Batch can be prepared with minimal asphaltene instability risk.

Notes for Blend 3: Blend CPH ~14. Too low. Recommend not to prepare this batch, adjust component content as required.

The invention claimed is:

1. A method for preparing a visbroken residue stream of interest in a refinery process, the precipitation of asphaltenes prevented from the visbroken residue stream of interest, said method comprising:

comparing solvent power of the visbroken residue stream of interest, $SP_{VisRes(OI)}$, with critical solvent power of the visbroken residue stream of interest, $CSP_{VisRes(OI)}$, categorizing the visbroken residue stream of interest as unstable if $SP_{VisRes(OI)}$ is not greater than $CSP_{VisRes(OI)}$, and if $SP_{VisRes(OI)}$ is not greater than $CSP_{VisRes(OI)}$, adjusting the refinery process to provide the visbroken residue stream of interest with a value of $SP_{VisRes(OI)}$ that is greater than $CSP_{VisRes(OI)}$, wherein $CSP_{VisRes(OI)}$ is predicted from the critical percentage titrant for asphaltene stability in an atmospheric residue stream, $CPT_{AR(OI)}$, the atmospheric residue stream of interest being derived from the same crude oil as the visbroken residue stream of interest, using a correlation obtained by a method comprising:

for each of a plurality of crude oils, determining:
$CSP_{VisRes}$ of a visbroken residue stream derived therefrom, and
$CPT_{AR}$ of an atmospheric residue stream derived therefrom, and
determining a correlation between $CSP_{VisRes}$ and $CPT_{AR}$.

$SP_{VisRes(OI)}$ is predicted using the following formula:

$$SP_{VisRes(OI)} = (100 \times CSP_{VisRes(OI)})/(100 - CPT_{VisRes})$$

wherein:
$CPT_{VisRes}$ is the critical percentage titrant (vol %) for asphaltene stability in the visbroken residue stream, wherein $CPT_{VisRes}$ is derived from the critical percentage cetane (vol %) for asphaltene stability in the visbroken residue stream, $CPC_{VisRes}$ using the following formula:

$$CPT_{VisRes} = CF + CPC_{VisRes}$$

wherein:
CF is a conversion factor that relates $CPT_{VisRes}$ to $CPC_{VisRes}$,
and wherein $CPC_{VisRes}$ is calculated from the P-value of the visbroken residue stream using the following formula:

$$CPC_{VisRes} = ([(P\text{-value}-1)^*\rho_{VisRes}]/[((P\text{-value}-1)^*\rho_{VisRes})+1])^*100$$

wherein:
$\rho_{VisRes}$ is the density of the visbroken residue stream.

2. The method of claim 1, wherein adjusting the refinery process comprises one or more of: modifying a feed inputted into a visbreaker unit (VSB), and modifying conditions in the VSB.

3. The method of claim 1, wherein $CPT_{AR}(O_I)$ is predicted using the following formula:

$$CPT_{AR} = 100 - (100^*CPS_{AR})/SP_{AR}$$

wherein:
$CSP_{AR}$ is the critical solvent power of the atmospheric residue, and
$SP_{AR}$ is the solvent power of the atmospheric residue.

4. The method of claim 3, wherein $CSP_{AR}$ is assumed to be equal to the critical solvent power of the crude oil from which the atmospheric residue is derived.

5. The method of claim 3, wherein $SP_{AR}$ is obtained by a method comprising:
titrating a precipitant against at least two samples of the atmospheric residue diluted with different amounts of solvent to determine a volume fraction of the atmospheric residue at the onset of asphaltene precipitation, $V_{(onset\ fraction\ AR)}$, and a volume fraction of the solvent at the onset of asphaltene precipitation, $V_{(onset\ fraction\ S)}$; and deriving $SP_{AR}$ from a linear correlation between $SP_S*V_{(onset\ fraction\ S)}$ and $V_{(onset\ fraction\ AR)}$ based on the following formula:

$$SP_{AR} = \frac{(CSP_{AR} - SP_S * V_{(onset\ fraction\ S)})}{V_{(onset\ fraction\ AR)}}$$

wherein:
$CSP_{AR}$ is the critical solvent power of the atmospheric residue, and
$SP_S$ is the solvent power of the solvent.

6. The method of claim 1, wherein the method for predicting $CSP_{VisRes(OI)}$ comprises:
predicting $CSP_{VisRes(OI)}$ from the critical percentage titrant for asphaltene stability in an atmospheric residue stream, $CPT_{AR(OI)}$, derived from the same crude oil as the visbroken residue stream, and the ratio of feed rate to coil outlet temperature (COT) of visbreaker unit (VSB) in which the visbroken residue of interest is produced,
wherein the method for obtaining a correlation between $CPT_{AR}$ and $CSP_{VisRes}$ comprises:
assigning each of the plurality of crude oils to a subgroup based on the ratio of the feed rate to COT of the VSB in which the visbroken residue is produced, and
determining a correlation between $CPT_{AR}$ and $CSP_{VisRes}$ for each subgroup.

7. The method of claim 1, wherein the P-value for the visbroken residue stream is in the range of from 1.05 to 1.30.

8. The method of claim 1, wherein CF is determined using a method which comprises measuring $CPT_{VisRes}$ and $CPC_{VisRes}$ for a plurality of visbroken residue streams; and deriving the conversion factor, CF, that relates $CPT_{VisRes}$ to $CPC_{VisRes}$.

9. The method of claim 1, wherein $CPT_{VisRes}$ is the critical percentage titrant, the titrant being selected from $C_{5-8}$ n-alkanes or $C_{5-8}$ iso alkanes.

10. A method for preparing a fuel oil in a refinery process, the precipitation of asphaltenes prevented from the fuel oil, the fuel oil containing n blend components including a visbroken residue stream of interest, said method comprising:
in a refinery process, visbreaking a residue stream to provide the visbroken residue stream of interest,
comparing solvent power of the fuel oil, $SP_{FO}$, with critical solvent power of the fuel oil, $CSP_{FO}$,
categorizing the fuel oil as unstable if $SP_{FO}$ is not greater than $CSP_{FO}$, and
if $SP_{FO}$ is not greater than $CSP_{FO}$, adjusting the refinery process and blending the visbroken residue stream of interest with the n-1 other blend components to provide the fuel oil to produce a fuel oil for which $SP_{FO}$ is greater than $CSP_{FO}$,
wherein
$CSP_{FO}$ is predicted using the following formula:

$$CSP_{FO} = \sum_{i=1}^{n} \frac{(Wt\ \%_i * Asp\ content_i)}{Asp\ content_{(FO)}} * CSP_i$$

wherein:
Wt %, is the % by weight, of each of the n blend components
Asp content, is the asphaltene content of each of the n blend components,
Asp content$_{(FO)}$ is the asphaltene content of the fuel oil, and
$CSP_i$ is the critical solvent power of each of the n blend components,
$SP_{FO}$ is predicted using the following formula:

$$SP_{FO} = \sum_{i=1}^{n} Vol\ \%_i * SP_i$$

wherein:
Vol %, is the % by volume of each of the n blend components in the fuel oil, and
$SP_i$ is the solvent power of each of the n blend components,
and wherein
the critical solvent power of a visbroken residue stream of interest, $CSP_{VisRes(OI)}$, is predicted from the critical percentage titrant for asphaltene stability in an atmospheric residue stream, $CPT_{AR(OI)}$, the atmospheric residue stream being derived from the same crude oil as the visbroken residue stream, using a correlation obtained by a method comprising:
for reach of a plurality of crude oils, determining:
$CSP_{VisRes}$ of a visbroken residue stream derived therefrom, and
$CPT_{AR}$ of an atmospheric residue stream derived therefrom, and
determining a correlation between $CSP_{VisRes}$ and $CPT_{AR}$; and
the solvent power of a visbroken residue stream of interest, $SP_{VisRes(OI)}$, is predicted using the following formula:

$$SP_{VisRes(OI)} = (100 \times CSP_{VisRes(OI)} / (100 \times CPT_{VisRes})$$

wherein $CPT_{VisRes}$ is the critical percentage titrant (vol %) for asphaltene stability in the visbroken residue stream, and wherein $CPT_{VisRes}$ is derived from the critical percentage cetane (vol %) for asphaltene stability in the visbroken residue stream, $CPC_{VisRes}$ using the following formula:

$$CPT_{VisRes} = CF + CPC_{VisRes}$$

wherein:
CF is a conversion factor that relates $CPT_{VisRes}$ to $CPC_{VisRes}$,
and wherein $CPC_{VisRes}$ is calculated from the P-value of the visbroken residue stream using the following formula:

$$CPC_{VisRes} = ([(P\text{-value}-1)*\rho_{VisRes}] / [((P\text{-value}-1)*\rho_{VisRes})+1]) * 100$$

wherein:
$\rho_{VisRes}$ is the density of the visbroken residue stream.

11. The method of claim 10, wherein adjusting the refinery process comprises one or more of: modifying a feed inputted into a visbreaker unit (VSB), modifying conditions in the VSB, adjusting the amount or type of cutter stocks that are added to the visbroken residue stream of interest, and changing fuel oil or fuel oil blend.

12. The method of claim 10, wherein $CPT_{AR}(O_I)$ is predicted using the following formula:

$$CPT_{AR}=100-(100*CSP_{AR})/SP_{AR}$$

wherein:
$CSP_{AR}$ is the critical solvent power of the atmospheric residue, and
$SP_{AR}$ is the solvent power of the atmospheric residue.

13. The method of claim 12, wherein $CSP_{AR}$ is assumed to be equal to the critical solvent power of the crude oil from which the atmospheric residue is derived.

14. The method of claim 12, wherein $SP_{AR}$ is obtained by a method comprising:
titrating a precipitant against at least two samples of the atmospheric residue diluted with different amounts of solvent to determine a volume fraction of the atmospheric residue at the onset of asphaltene precipitation, $V_{(onset\ fraction\ AR)}$, and a volume fraction of the solvent at the onset of asphaltene precipitation, $V_{(onset\ fraction\ S)}$; and
deriving $SP_{AR}$ from a linear correlation between $SP_S*V_{(onset\ fraction\ S)}$ and $V_{(onset\ fraction\ AR)}$ based on the following formula:

$$SP_{AR} = \frac{(CSP_{AR} - SP_S * V_{(onset\ fraction\ S)})}{V_{(onset\ fraction\ AR)}}$$

wherein:
$CSP_{AR}$ is the critical solvent power of the atmospheric residue, and
$SP_S$ is the solvent power of the solvent.

15. The method of claim 10, wherein the method for predicting $CSP_{VisRes(OI)}$ comprises:
predicting $CSP_{VisRes(OI)}$ from the critical percentage titrant for asphaltene stability in an atmospheric residue stream, $CPT_{AR(OI)}$, derived from the same crude oil as the visbroken residue stream, and the ratio of feed rate to coil outlet temperature (COT) of visbreaker unit (VSB) in which the visbroken residue of interest is produced,
wherein the method for obtaining a correlation between $CPT_{AR}$ and $CSP_{VisRes}$ comprises:
assigning each of the plurality of crude oils to a subgroup based on the ratio of the feed rate to COT of the VSB in which the visbroken residue is produced, and
determining a correlation between $CPT_{AR}$ and $CSP_{VisRes}$ for each subgroup.

16. The method of claim 10, wherein the P-value for the visbroken residue stream is in the range of from 1.05 to 1.30.

17. The method of claim 10, wherein CF is determined using a method which comprises measuring $CPT_{VisRes}$ and $CPC_{VisRes}$ for a plurality of visbroken residue streams; and deriving the conversion factor, CF, that relates $CPT_{VisRes}$ to $CPC_{VisRes}$.

18. The method of claim 10, wherein $CPT_{VisRes}$ is the critical percentage titrant, the titrant being selected from $C_{5-8}$ n-alkanes or $C_{5-8}$ iso alkanes.

* * * * *